United States Patent
Prichard et al.

[11] Patent Number: 5,830,401
[45] Date of Patent: Nov. 3, 1998

[54] METHOD OF MANUFACTURING A CATHETER/HUB STRAIN RELIEF

[75] Inventors: James B. Prichard, St. Peters; Raymond O. Bodicky, Oakville, both of Mo.

[73] Assignee: Sherwood Medical Company, St. Louis, Mo.

[21] Appl. No.: 201,591

[22] Filed: Feb. 25, 1994

Related U.S. Application Data

[62] Division of Ser. No. 911,599, Jul. 10, 1992, Pat. No. 5,380,301.

[51] Int. Cl.⁶ .......................... B29C 45/14; B29C 45/36
[52] U.S. Cl. ..................... 264/262; 264/261; 264/266; 264/267; 264/275
[58] Field of Search ..................... 264/259, 266, 264/267, 275, 261, 263, 262; 156/86, 211; 604/281, 283

[56] References Cited

U.S. PATENT DOCUMENTS

| | | |
|---|---|---|
| 3,097,646 | 7/1963 | Scislowicz . |
| 3,191,655 | 6/1965 | McCord ................................. 264/263 |
| 3,469,579 | 9/1969 | Hubert . |
| 3,720,210 | 3/1973 | Diettrich . |
| 3,721,231 | 3/1973 | Hubert ................................. 604/283 |
| 3,802,433 | 4/1974 | Raven ................................. 604/283 |
| 3,861,972 | 1/1975 | Glover et al. ......................... 156/86 |
| 4,191,185 | 3/1980 | Lemieux ............................... 604/283 |
| 4,211,741 | 7/1980 | Ostoich ................................. 264/173 |
| 4,292,970 | 10/1981 | Hession, Jr. .......................... 604/157 |
| 4,354,495 | 10/1982 | Bodicky ............................... 604/283 |
| 4,389,210 | 6/1983 | Genese ................................. 604/177 |
| 4,391,029 | 7/1983 | Czuba et al. ........................... 29/450 |
| 4,592,749 | 6/1986 | Ebling et al. .......................... 604/283 |
| 4,610,674 | 9/1986 | Suzuki et al. ......................... 604/282 |
| 4,776,849 | 10/1988 | Shinno et al. ......................... 604/283 |
| 4,781,703 | 11/1988 | Walker et al. ......................... 604/264 |
| 4,806,182 | 2/1989 | Rydell et al. .......................... 156/211 |
| 4,840,622 | 6/1989 | Hardy ................................. 604/264 |
| 4,846,812 | 7/1989 | Walker et al. ......................... 604/264 |
| 4,966,588 | 10/1990 | Rayman et al. ....................... 604/165 |
| 4,991,629 | 2/1991 | Ernesto et al. ........................ 138/89 |
| 5,030,205 | 7/1991 | Holdaway et al. ..................... 604/164 |
| 5,041,097 | 8/1991 | Johnson ............................... 604/167 |
| 5,167,647 | 12/1992 | Wijkamp et al. ..................... 604/281 |

FOREIGN PATENT DOCUMENTS

| | | |
|---|---|---|
| 1125735 | 7/1956 | France . |
| 2033068 | 11/1970 | France . |

Primary Examiner—Jan H. Silbaugh
Assistant Examiner—Angela Ortiz
Attorney, Agent, or Firm—Gene B. Kartchner; David A. Warmbold; Montgomery W. Smith

[57] ABSTRACT

A catheter is disclosed which includes a mechanical connection between the strain relief thereof and the hub. The strain relief operates both to secure the catheter tube to the hub and to provide strain relief for the catheter tube. The strain relief connection is assisted in gripping the catheter tube by intentional overstressing of the catheter hub during manufacture thereof to expand the hub wall and generate residual hoop stresses therein which assist in securing the catheter tube within the hub.

7 Claims, 3 Drawing Sheets

METHOD OF MANUFACTURING A CATHETER/HUB STRAIN RELIEF

This is a divisional of application Ser. No. 07/911,599 filed on Jul. 10, 1992, now U.S. Pat. No. 5,380,301.

BACKGROUND OF THE INVENTION

1. Field of the Invention

This invention relates generally to catheters. More specifically, the present invention relates to a method of attaching a catheter hub to the end of a catheter tube, and an improvement in strain relief therebetween.

2. Prior Art

Medical catheters generally comprise a flexible catheter tube which is permanently attached at one end to a rigid hub. The hub functions as a connector to allow quick connection of a syringe or the like to the catheter. Because bending forces applied to the catheter tube tend to be concentrate at the hub/catheter tube juncture, a strain relief is usually incorporated into the hub/catheter tube juncture to help avoid collapse of the catheter tube due to these periodic force concentrations which occur during use.

Strain relief devices are traditionally formed of a material which is more flexible than the hub and less flexible than the catheter tube. The strain relief device is generally formed of a sufficient length to allow attachment of one end thereof to the hub while allowing the opposite end to extend a substantial distance along the catheter tube beyond the hub/catheter tube juncture. With such a strain relief device in place, bending forces applied to the tube at the juncture area are resisted by the strain relief device and prevented from concentrating sufficiently at the juncture to cause collapse of the catheter tube. The strain relief device thereby functions to "relieve" the strain at the juncture by spreading bending forces along a larger length of the catheter tube.

Although strain relief devices of this type have in the past functioned adequately to relief the strain of bending forces at a hub/catheter tube juncture, they have nevertheless failed to aid in strengthening the juncture against axial forces, i.e., forces along the longitudinal axis of the catheter tube which tend to pull the catheter tube away from the hub nor significantly aided in forming or strengthening the hub/catheter tube attachment itself. Longitudinal ("pulling") forces can arise during the use of a catheter through any number of commonly occurring accidents or mishaps, and can lead to disastrous consequences for a patient who may heavily rely on the proper functioning of the catheter.

For example, serious if not fatal consequences can result from incidental hub/catheter tube separation when the catheter is in use in a patient, especially when the catheter is placed within an artery or vein. A release of the catheter tube subsequent to separation from its hub can actually resulted in the catheter tube becoming lost in the patient's cardiovascular system. Alternatively, the incidental separation of a catheter tube from its hub, if gone unnoticed, may prevent the infusion of important medicaments or other fluids into a patient. Obviously, in each instance the results can be disastrous for the patient.

A major manufacturing problem occurring with prior art catheters which makes it difficult to form a strain relief which can also inhibit separation due to pulling forces as well as prevent kinking due to bending forces includes the difficulty in securely attaching the relatively flexible catheter tube of a particular polymeric material to the relatively rigid hub of different polymeric material in a secure manner.

Secure catheter tube/hub attachment is especially problematic since many polymeric materials are incompatible for secure and reliable attachment by adhesive, solvent, heat, or other chemical bonding. It can be necessary therefore to attach the catheter tube to the hub by means of a mechanical attachment, which is apart from and in addition to the strain relief, and which functions independently of the strain relief to inhibit separation due to pulling forces.

Czuba et al., U.S. Pat. No. 4,391,029, is exemplary of prior art catheter assemblies which include the attachment of a catheter tube to a hub by means of a mechanical attachment which is separate and in addition to the strain relief. Czuba et al.'s catheter includes a catheter tube end which is enlarged relative to the remainder of the catheter tube, and which is sized to fit within the hub. A rigid tubular funnel is inserted into the lumen of the catheter tube to prevent any subsequent collapse and/or passage of the enlarged end of the catheter tube through the relatively constricted portion of the hub should there be an attempt to pull the catheter out of the hub. As can be seen in the Czuba et al. patent, the strain relief of the Czuba et al. device is completely separate from the enlarged end of the catheter tube and the rigid tubular funnel.

Prior art catheter/hub connection methods such as described in Czuba et al. above, while functioning well to prevent inadvertent separation of the catheter tube and hub, nevertheless are somewhat difficult to manufacture and relatively expensive due to the added elements and materials used, and due to the manufacturing procedures necessitated thereby.

There therefore exists a need in the art to develop a catheter having a catheter tube/hub connection which is inexpensive in materials and manufacturing, and which can secure the connection therebetween regardless of the materials composing the catheter tube or the hub, in a secure inseparable relationship. Further, there exists a need in the art to develop a strain relief between a catheter tube and hub which can function both to prevent inadvertent kinking or bending of the catheter tube while in use, and to inhibit separation due to applied longitudinal pulling forces.

OBJECTS AND SUMMARY OF THE INVENTION

It is an object of the present invention to provide a method of manufacturing a catheter which includes attachment of a catheter tube to a hub in a secure manner to prevent separation of the catheter tube from the hub during use.

It is another object of the present invention to provide a method of manufacturing a catheter which allows secure attachment of a catheter tube to a hub by the strain relief, even though the strain relief and hub are made of materials which would be incompatible for attachment as by an adhesive or solvent bonding process.

It is a further object of the present invention to provide a catheter having a strain relief which mechanically attaches with the hub in such a manner that attachment forces tend to increase whenever separation forces such as longitudinal pulling forces are applied thereto.

It is also an object of the present invention to provide a method of manufacturing a catheter which includes an insert molding procedure in which an insert molding is formed about the catheter tube and hub to form the attachment therebetween.

It is also an object of the present invention to provide a method of manufacturing a catheter in which the insert molding process which forms the attachment between the catheter tube and hub also forms the strain relief therefore.

These and other objects and advantages are realized in a presently preferred embodiment of the present invention, which is shown by way of example and not necessarily by way of limitation, of a catheter which includes a hub member formed to include a basket shaped extension on the distal end thereof having a plurality of uniformly spaced longitudinally directed ribs forming openings therethrough which extend from the distal end of the hub member to a generally annular end piece, with the end piece forming a central cylindrical opening therein which is slightly larger than the outer diameter of the catheter tube which is to be adjoined with the hub.

The catheter also includes a catheter tube which is connected to the hub by an insert molding process in which the catheter tube is positioned within the opening of the end piece of the hub to extend along the internal bore of the hub, and a core pin is then inserted into the proximal end of the hub through the lumen of the catheter tube to seal the interior of the catheter tube and the bore of the hub proximal of the catheter tube. The hub, catheter tube and core pin are then inserted into a mold and material is injected through the openings between the ribs of the basket of the hub and form along the hub bore between the exterior of the catheter tube and the interior surface of the hub bore, to be stopped only by the core pin. The injection mold also includes formation of an outer extension which extends around a portion of the exterior of the hub end beyond the distal end of the hub a specified length along the exposed catheter tube to complete the formation of the strain relief.

Due to the presence of a relief cavity in the mold, injection of the molding material into the mold causes a portion of the bore of the hub to be enlarged in its internal diameter. Upon cooling of the injection material, the resultant forces caused by the hub wall attempting to contract to its original shape and the resulting forces caused by cooling of the injected material, generate a very strong mechanical grip along the catheter tube. Due to the effect of the interior shape of the hub bore on the injected material forming the strain relief and residual hoop stresses in the hub wall caused by its expansion, subsequent attempts to withdraw the catheter tube from the hub cause an increase in the gripping forces applied against the catheter tube by the strain relief.

The mechanical-type attachment between the strain relief and the hub of the present invention allows the strain relief and hub to be formed of materials which may otherwise be incompatible for other types of attachment, such as adhesive or bonding type attachment.

DETAILED DESCRIPTION OF THE INVENTION

Figure 1:
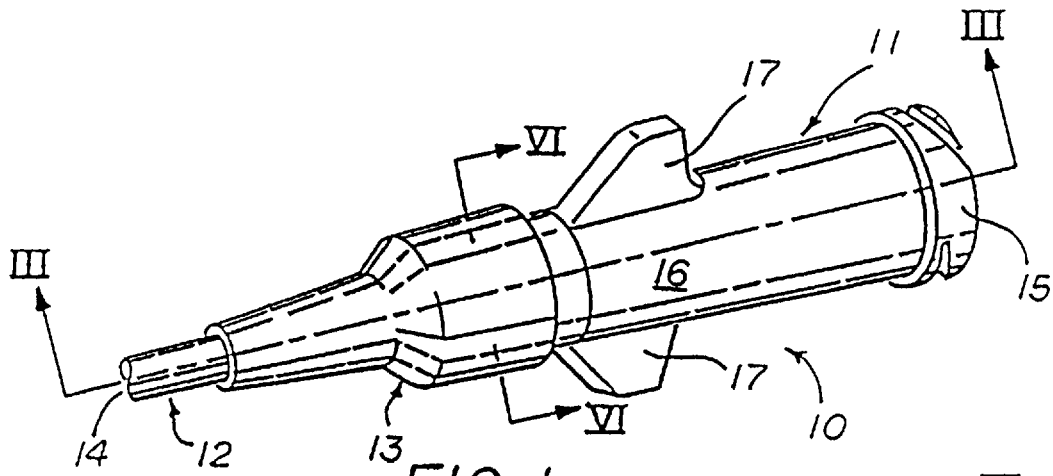
FIG. 1 shows a perspective view of a catheter formed in accordance with the principles of the present invention.

As shown in the exemplary drawings for the purposes of illustration, an embodiment of a catheter made in accordance with the principles of the present invention, referred to generally by the reference numeral 10, is provided which includes attachment of a catheter tube to a hub through insert molding of a strain relief attachment in such a manner that resultant forces between the strain relief and hub form a mechanical attachment which increase its gripping force in response to attempted withdrawal of the catheter tube from the hub.

More specifically, as shown in FIG. 1, the catheter 10 of the present invention includes a hub 11 and a catheter tube 12 surrounded at their juncture by a strain relief 13. The catheter tube 12 is preferably formed of a fairly soft flexible PVC or polyurethane having a relatively low durometer hardness, and includes one or more lumens 14 formed therein. The hub 11 is formed of a more rigid material, preferably polypropylene, having a relatively high durometer hardness.

The strain relief 13 is preferably formed of a material such as polyurethane or PVC having a flexibility and durometer hardness which is preferably greater than that of the tube 12, yet less than that of the hub 11. The strain relief 13 is molded about the catheter tube 12 and hub 11 in a manner as will be explained in detail below, so as to form a mechanical connection between the hub and the strain relief 13 which does not rely on compatibility of the materials forming the strain relief 13 or hub 11 for secure attachment as do adhesive or solvent bonding type connections of many prior art devices. The attachment between the catheter tube 12 and the strain relief 13 may also be mechanical in nature or may be partly formed by slight mixing of materials therebetween during the injection molding process, or a combination of both attachment types.

Figure 2:
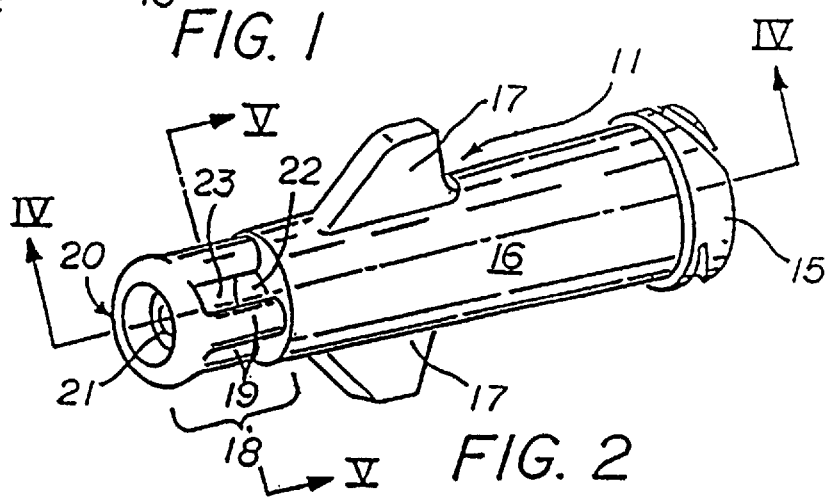
FIG. 2 shows a perspective view of a catheter hub formed in accordance with the principles of the present invention.

As best shown in FIG. 2, the hub 11 is formed to a slightly tapering generally elongate cylindrical shape and includes a fitting 15 on the proximal end thereof for attachment to a syringe or the like in a well known manner. The fitting 15 as shown includes a threaded attachment, however any well known fitting used for attaching a hub to a syringe or other medical device useful with catheters is anticipated by the present invention and would be considered an obvious substitution for the fitting 15. The hub 11 is formed of a generally smooth tapered outer surface 16 on which is preferably formed a pair of wing members 17 useful as gripping surfaces to assist a user in attaching the hub 11 to a syringe or the like.

Figure 4:
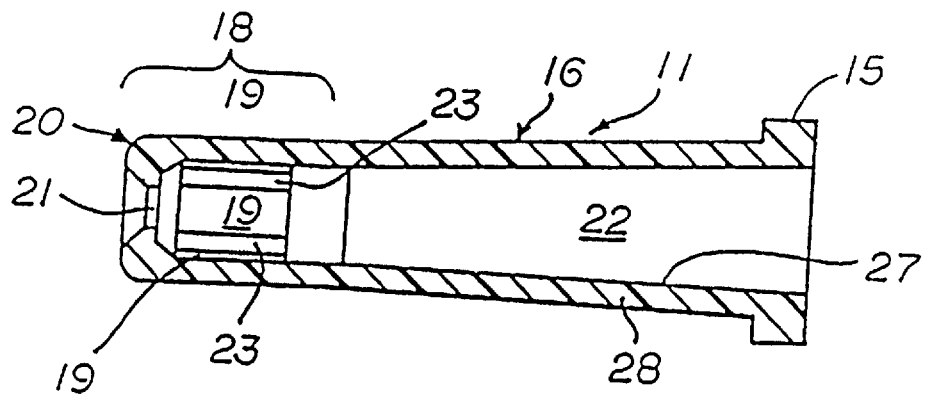
FIG. 4 shows a cross-sectional view of the catheter hub taken along line IV—IV of FIG. 2.

The distal end of the hub 11 has a longitudinally extending basket 18 formed thereon which includes preferably four longitudinally extending ribs 19 joined together at their distal ends by an annular end piece 20. As best shown in FIGS. 2 and 4, the annular end piece 20 has formed therein a central cylindrical opening 21 which is positioned coaxially with the central longitudinal axis of the hub 11.

As shown in FIG. 4, the hub 11 forms a bore 22 which is generally cylindrical within the area of the basket 18, and is slightly tapered from the proximal end of the hub 11 to adjacent the basket 18.

Figure 5:
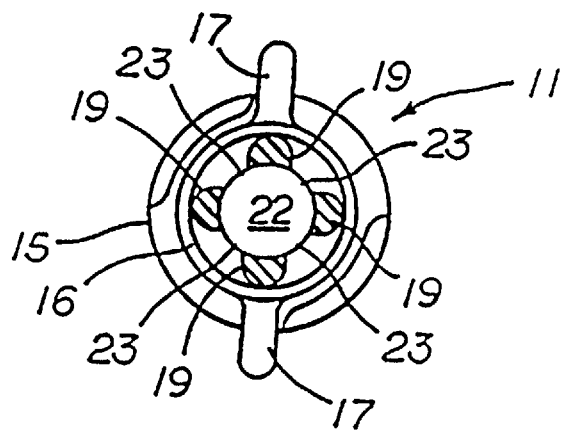
FIG. 5 is a cross-sectional view of the catheter hub taken along line V—V of FIG. 2.

As is best shown in FIG. 5, the ribs 19 of the basket 18 are separated to form openings 23 into the bore 22. These openings 23 allow injection molding material to freely pass through the basket 18 into the bore 22 of the hub 11 during manufacture of the strain relief 13 as will be explained below.

It should be understood that the main purpose of the basket 18 is to form openings such as openings 23 through the hub 11 into the bore 22 through which injected molding material forming the strain relief 13 can pass. The present invention is not intended to be limited to the basket 18 as described with respect to the preferred embodiment only except to the extent wherein the hub 11 includes at least one opening therein, independent of the opening through which the catheter tube 12 is placed, through which injected material may pass. Also, although it is preferred that no loose ends extend from the distal end of the hub 11, the annular end piece 20 need not necessarily be present, or may be extensively modified. The main purpose of the annular end piece 20 is to assist in holding the catheter tube 12 in a central position within the hub 11 during movement of injection material into the bore 22.

Figure 3:
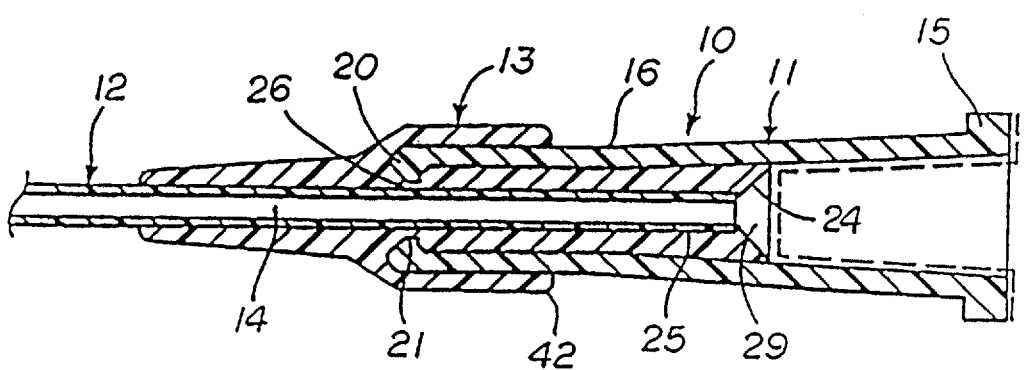
FIG. 3 shows a cross-sectional view of the catheter taken along line III—III of FIG. 1.

As shown in FIG. 3, the strain relief 13 is formed about the catheter tube 12 and the hub 11, and extends along the catheter tube 12 a predetermined distance from the distal end of the hub 11 in order to provide support to the catheter tube 12 against kinking thereof due to bending forces during use. The strain relief 13 also extends within the bore 22 of the hub 11 and secures the entire portion of the catheter tube 12 enclosed within the bore 22.

The proximal end of the strain relief 13 is formed into a conically shaped surface 24 directly adjacent the proximal end 25 of the catheter tube 12. The surface 24 is designed to be located within the hub 11 at a position which will cause it to be directly distal of the tip (shown in dashed lines) of any fully inserted male fitting of a syringe or the like, in order to limit as much as possible the volume of dead space 29 between the tip of the syringe or like device, and the distal end 25 of the catheter tube 12. The minimization of the total volume of dead space 29 helps minimize distortion, and improve signal response of real time fluid pressure measurements which may be performed with the aid of the catheter 10.

Figure 6:
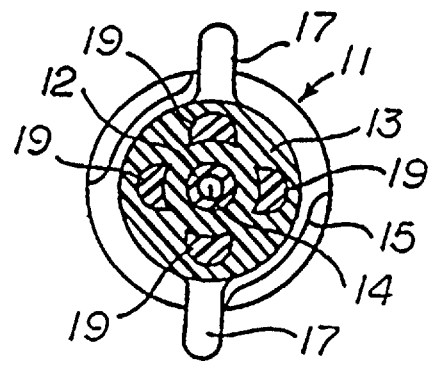
FIG. 6 is a cross-sectional view of the catheter taken along line VI—VI of FIG. 1.

The strain relief 13 is formed in continuous contact with the catheter tube 12 along the entire length of the strain relief 13 including the clearance area 26 between the catheter tube 12 and the central cylindrical opening 21 of the annular end piece 20. Also, as can be seen in FIG. 6, the strain relief 13 completely encapsulates the ribs 19 of the basket 18 of the hub 11. This integral interconnection between the hub 11 and the strain relief 13 permanently fixes the strain relief 13 relative to the hub 11 without any necessity of adhesive or solvent bonding material. As will be explained below with respect to the method of manufacturing of the catheter 10 of the present invention, the strain relief 13 securely grips the catheter tube 12 due to residual hoop stresses in the hub wall 28 and residual contraction forces within the strain relief 13. Further, fluid pressure against the conical proximal surface 24 which may be caused by injection of fluid into the dead space 29 by a syringe or the like, will cause a force along the cylindrical wedged portion of the strain relief 13 within the bore 22. This force also tends to increase the gripping force of the strain relief 13 against the catheter tube 12.

The method of manufacture of the catheter 10 of the present invention is as follows.

Figure 7:
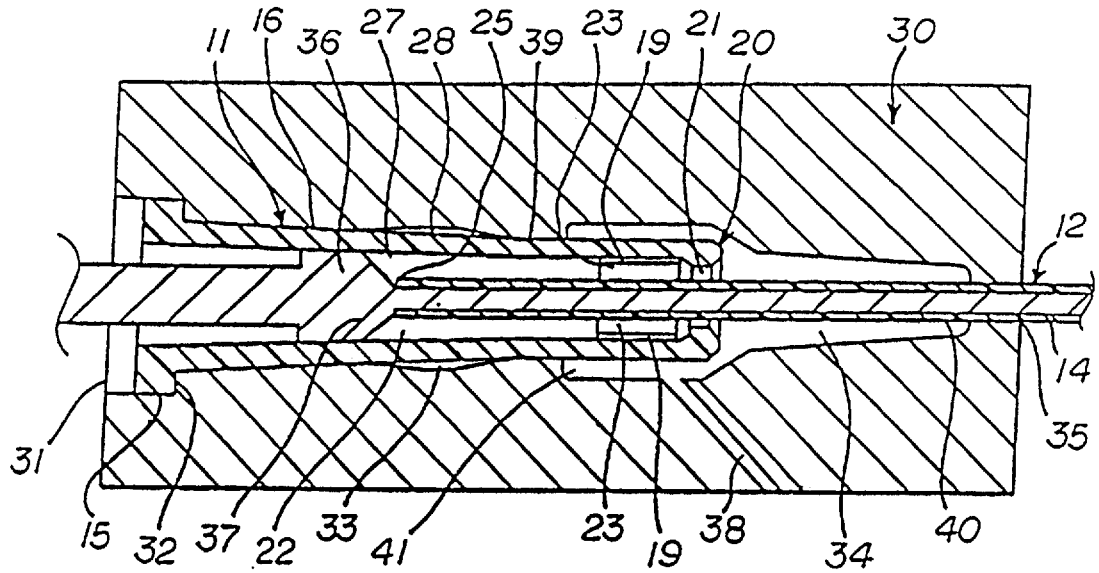
FIG. 7 is a cross-sectional view of a catheter tube and hub properly positioned in an insertion molding apparatus including a core pin placed through the catheter tube; and, FIG. 8 is a cross-sectional view of the same apparatus shown in FIG. 7 after molding material forming the attachment and strain relief, has been injected into the mold cavity.

FIG. 7 shows a cross section of a mold 30 which is formed to allow insert molding of the strain relief 13 about the hub 11 and catheter tube 12.

The catheter tube 12 is inserted into the hub 11 so as to pass directly through the central cylindrical opening 21 in the annular end piece 20 and into bore 22 to a position approximately longitudinally adjacent the most proximal position of the cavity relief 33.

A core pin 36 is then inserted into the opening 31 of the mold 30 and through the lumen 14 of the catheter tube 12. The core pin 36 is of identical tapered dimension as the interior surface 27 of the bore 22, and forms a generally conical surface 37 which narrows the diameter of the core pin 36 to approximately the diameter of the lumen 14 of the catheter tube 12. As is clearly evident, the conical core pin surface 37 operates to form the conical proximal surface 24 of the strain relief 13 during the molding process.

As is shown, the hub 11, with catheter tube 12 and core pin 36 placed therein, is inserted into a first opening 31 in the mold 30 until the fitting 15 thereof abuts against shoulder 32 and the catheter tube 12 is pinched within the end opening 35. In this position, the external surface 16 of the hub 11 is completely surrounded and contacted by the mold 30 except at the position of cavity relief 33 and the distal end of the hub 11 which includes the basket 18. The remaining cavity 34 of the mold 30, as is clearly evident, is formed to the outer dimensions of the portion of the strain relief 13 which extends around the catheter tube 12 and the basket 18. Cavity 34 is designed to accept material used to mold the strain relief 13 while cavity relief 33 is designed to allow outward radial expansion of a portion of the hub wall 28 during molten material injection as will be explained momentarily.

The mold 30 also includes a gate 38 through which material forming the strain relief 13 is injected. The gate 38 is preferably formed at approximately a 45° angle from the longitudinal axis of the catheter hub 11 in order to minimize deflection of the catheter tube 12 due to the movement of injection material into the mold 30.

The mold 30 is formed to cause surfaces 39 and 40 to function as "shut off" surfaces against the passage of molding material in a well known manner. Also, the core pin 36 is designed to allow venting therepast, both through the proximal end of the hub 11 and through the bore 14 in a well known manner.

The cavity 34 extends to a position 41 which extends slightly beyond the most proximal position of the ribs 19 in the basket 18 in order to increase the length of the critical leak path of fluid. The "critical leak path" is defined as the most likely possible path of leakage of fluid past the strain relief 13 should leakage occur. This path would be the path taken by fluid injected into the dead space 29 which moved between the strain relief 13 and the inner surface 27 of the hub wall, and from there through the opening 23 between the ribs 19 and along the exterior surface 16 of the hub 11 until it escaped beyond the lip 42 of the strain relief 13. Although leakage along this path is very unlikely, the slight extension of the lip 42 in the proximal direction past the most proximal end of openings 23 tends to increase the critical leak path of the catheter 10, and thus reduce the possibility of leakage.

Figure 8:
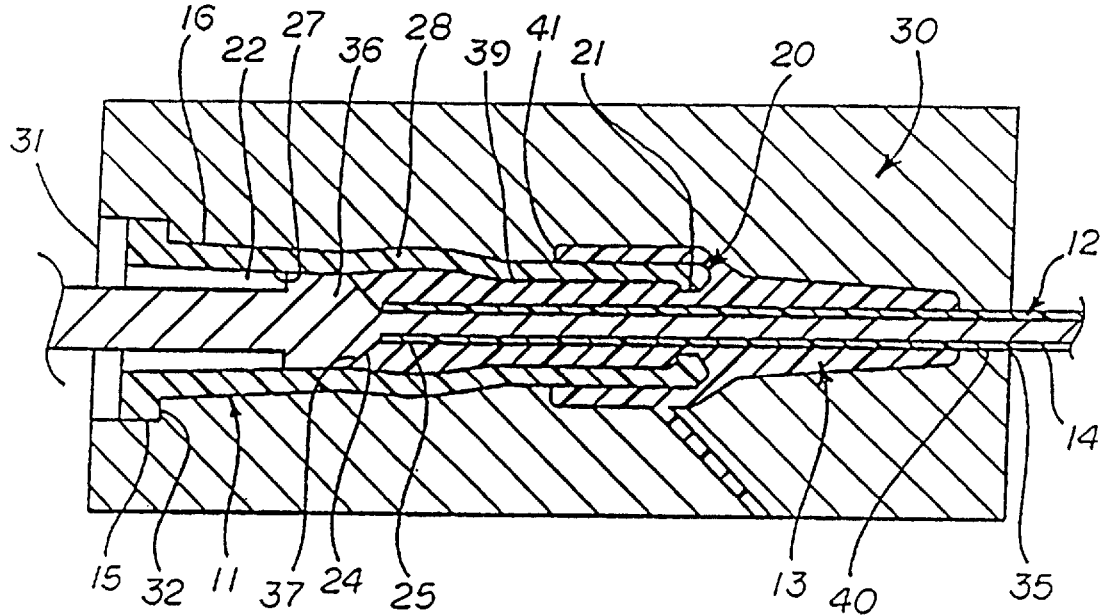

As best shown in FIG. 8, when material is injected into the cavity 34, it passes through the openings 23 of the basket 18 and into the bore 22. Further injection of material then completely fills the remainder of the cavity 34 to form the remainder of the strain relief 13. Excess pressure after complete filling of the cavity 34 causes the portion of the hub wall 28 adjacent the cavity relief 33 to be expanded into the cavity relief 33.

During cooling of the strain relief material, slight radial contraction thereof causes it to tighten around the basket 18 and also around the catheter tube 12. Further, cooling contraction in the longitudinal direction of the strain relief material located within the section of the hub core 22 which is slightly tapered in the distal direction, causes the catheter strain relief material to be drawn toward and wedged within the distal end of the hub 11, thus further increasing the gripping force of the strain relief 13 against the catheter tube 12. Also, residual hoop stresses within the expanded portion of the hub wall 28 exert continued contraction forces against the strain relief material adjacent thereto, which transfers through the adjacent strain relief material to also increase the gripping force against the catheter tube 12.

The cavity relief 33 is preferably formed of a series of flat annular surfaces which form a generally central location of greatest depth. The cavity relief 33 extends from a position parallel to the proximal most extent of the conical core pin surface 37 when properly positioned within the hub 11, to a position distal of the end 25 of the catheter tube 12. The cavity relief 33 is formed to a predetermined depth which will allow elastic expansion of the hub wall 28 thereinto but does not allow sufficient expansion of the hub wall 28 to cause permanent inelastic deformation thereof. The depth of the cavity relief 33 is preferably designed to allow an elastic expansion of the hub wall 28 equal to at least twice the expected radial shrinkage of the strain relief material during cooling, but no more than 50% of its elastic expansion limit.

The expansion of the hub wall 28 is intentionally designed to be at least twice the expected radial shrinkage of the strain relief material when cooled in order to allow the finished catheter 10 to have residual hoop stresses residing in the expanded portion of the hub wall 28 which can exert pressure on the strain relief 13 adjacent thereto to force it into a tight grip against the catheter tube 12. In this way, the radial shrinkage of the material forming the strain relief 13 during cooling thereof is compensated for by the residual hoop stresses in the wall 28 of the hub 11, and the longitudinal shrinkage of the material forming the strain relief 13 due to cooling is compensated for by the forced drawing or wedging of the material toward the distal end of the hub 11. Further, in use, pressure against the conical surface 24 caused by injection fluid also causes a wedging of the adjacent portions of the strain relief material into the distal end of the hub 11.

As is well known, over extended periods of time polymeric materials under stress will tend to "creep", meaning molecular movement on the microscopic level will occur which may cause some loss of residual stresses therein. The design of the catheter 10 of the present invention, due to the expansion of the hub wall 28 to several times the necessary expansion to compensate for the radial cooling contraction of the strain relief material is sufficient to ensure that residual hoop stresses remain in the hub 11 notwithstanding the long term effects of "creep" within the hub material.

Once the strain relief material is injected into the mold 30 to completely fill the cavity 34 and cause expansion of the hub wall 28 to fill the cavity 33, and the strain relief material has been allowed to cool, the catheter 10 is removed from the mold 30 and the core pin 36 is removed from the catheter 10.

As is evident, fluid pressure exerted against the conical proximal surface 24 of the strain relief 13 will force the portion of the strain relief 13 thereat, which is in the tapered area of the bore 22 of the hub 11, to be forced distally and further wedged into the narrowing diameter area of the core 22. The wedging effect caused by fluid pressure against the conical proximal surface 24 increases the gripping forces between the strain relief 13 and the catheter tube 12.

It is anticipated that any combination of hub and catheter tube materials may be used in the present invention, and attached by the strain relief 13 in the manner as described in the present method of manufacture, without regard to material composition compatibilities between the catheter tube 12, the strain relief 13, or the hub 11.

It will be apparent from the foregoing that, while particular embodiments of the invention have been illustrated and described, various modifications can be made thereto without departing from the spirit and scope of the invention. Accordingly, it is not intended that the invention be limited, except as by the appended claims.

We claim:

1. A method of manufacturing a catheter comprising the steps of:

placing a portion of a catheter tube within a bore of a hub means, molding an attachment means by injecting material into a mold cavity about and around a portion of the catheter tube such that a portion of the attachment means is molded within the hub means and another portion thereof extends distally of the hub means along and around the catheter tube to form a strain relief, said molding including forcing radial expansion of a portion of the hub means into a cavity relief area formed in the mold cavity by addition of excess material into the bore of the hub means.

2. A method according to claim 1 wherein said step of molding the attachment means includes inserting a portion of the catheter tube into the mold cavity before molding the attachment means.

3. A method according to claim 1 wherein the attachment means is molded through at least one opening in the hub means into the bore thereof.

4. A method according to claim 1 wherein the hub means includes a basket formed at a distal end thereof, the basket forms a plurality of openings therethrough into the bore of the hub, and said step of molding the attachment means includes filling the openings with molding material.

5. A method according to claim 1 further including the step of inserting a core pin into the bore of the hub means and through a lumen of the catheter tube before the step of molding the attachment means, and said step of molding the attachment means includes forming a tapered conical surface on the attachment means between the catheter tube and the inner surface of the hub means within the bore.

6. A method according to claim 1 wherein said step of forcing radial expansion of a portion of the hub means includes expanding the portion of the hub means with the excess material by at least twice the percentage of expected shrinkage of the attachment means due to cooling thereof but less than an amount which would cause overstretching at the hub.

7. A method according to claim 1 wherein the material forming the attachment means contracts upon cooling and thereby increases a gripping force between the attachment means and the catheter tube.

* * * * *